(12) United States Patent
Huang et al.

(10) Patent No.: US 11,780,883 B2
(45) Date of Patent: *Oct. 10, 2023

(54) DERIVED PEPTIDE OF LACTOFERRIN AND METHOD THEREOF FOR PROMOTING AND/OR INCREASING LIPID SYNTHESIS

(71) Applicant: RENORIGIN INNOVATION INSTITUTE CO., LTD., Taipei (TW)

(72) Inventors: Hsiu-Chin Huang, Taipei (TW); Hsuan Lin, Taipei (TW)

(73) Assignee: RENORIGIN INNOVATION INSTITUTE CO., LTD., Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 17/496,900

(22) Filed: Oct. 8, 2021

(65) Prior Publication Data

US 2023/0002449 A1 Jan. 5, 2023

(30) Foreign Application Priority Data

Jun. 30, 2021 (TW) .................................. 110123916

(51) Int. Cl.
*C07K 7/08* (2006.01)
*A61P 3/06* (2006.01)
*A61K 38/00* (2006.01)

(52) U.S. Cl.
CPC ..................... *C07K 7/08* (2013.01); *A61P 3/06* (2018.01); *A61K 38/00* (2013.01)

(58) Field of Classification Search
CPC ............. C07K 7/08; A61P 3/06; A61K 38/00
See application file for complete search history.

(56) References Cited

U.S. PATENT DOCUMENTS 7,026,295 B2 * 4/2006 Varadhachary ........ A61K 38/40
435/7.1
2015/0139955 A1 * 5/2015 Oda .......................... A61P 1/00
514/21.4

OTHER PUBLICATIONS

Ling et al., 2019, Lactoferrin promotes bile acid metabolism and reduces hepatic cholesterol deposition by inhibiting the farnesoid X receptor (FXR)-mediated enterohepatic axis, Food & Function, 10: 7299-7307.*
Guo et al., 2020, Recombinant human lactoferrin attenuates the progression of hepatosteatosis and hepatocellular death by regulating iron and lipid homeostasis in ob/ob mice, Food & Function, 11: 7183-7196.*
Kim et al., 2010, Dietary effect of lactoferrin-enriched fermented milk on skin surface lipid and clinical improvement of acne vulgaris, Nutrition, 26: 902-909.*
Xiong et al., 2018, Lactoferrin attenuates high-fat diet-induced hepatic steatosis and lipid metabolic dysfuctions by suppressing hepatic lipogenesis and down-regulating inflammation in C57BL/6J mice, Food & Function, 9: 4328-4339.*
Appelmelk et al., 1994, Lactoferrin Is a Lipid A-Binding Protein, Infection and Immunity, 62(6): 2628-2632.*

* cited by examiner

*Primary Examiner* — Amber D Steele
(74) *Attorney, Agent, or Firm* — Birch, Stewart, Kolasch & Birch, LLP

(57) ABSTRACT

The present invention provides a derived peptide of a lactoferrin, a composition comprising the same and a use thereof for promoting and/or increasing lipid synthesis. The derived peptide of the lactoferrin comprises the amino acid sequence of SEQ ID NO: 01.

4 Claims, 2 Drawing Sheets

Specification includes a Sequence Listing.

DERIVED PEPTIDE OF LACTOFERRIN AND METHOD THEREOF FOR PROMOTING AND/OR INCREASING LIPID SYNTHESIS

BACKGROUND OF THE INVENTION

Field of the Invention

The present invention relates to a derived peptide of a lactoferrin, a composition comprising the same and a method thereof and, in particular, to a derived peptide of a lactoferrin, a composition comprising the same and a method thereof for promoting and/or increasing lipid synthesis.

Description of the Prior Art

The sebaceous glands of the scalp secrete sebum, forming a sebum film attached to the scalp stratum corneum. This layer of sebum film can retain water and form a moist, nutritious environment that is conducive to the survival of microorganisms. The quality of the scalp will be affected by factors such as immunity, epidermal shielding, genetics, mood, nutrition, pH, and moisture, which in turn affects the amount of lipid (sebum) secreted.

When the sebaceous glands are interfered by the organism itself and the external environment, the function of the sebaceous glands in regulating lipid secretion is weakened, and the sebaceous glands cannot properly regulate the secretion of lipid. For example, aging, excessive use of cleansing shampoos, long-term exposure to ultraviolet rays, or dry conditions in winter may all be the cause of less lipid secretion by sebaceous glands. When the sebum secretion is insufficient to form a complete sebum film to protect the scalp, it will cause damage to the epidermal layer of the scalp or loss of water, making the scalp dry, itchy, rough, and dull, erythema, or even dry desquamation in appearance. (Abramovits W, Gonzalez-Serva A. Sebum, cosmetics, and skin care. *Dermatol Clin.* 2000; 18(4):617-620. doi:10.1016/S0733-8635(05)70212-6).

In order to solve the problem of too little lipid secretion by the sebaceous glands, there are therapeutic drugs on the market. In the case of external medicines, generally anti-inflammatory ingredients, anti-itching ingredients, skin tissue repair ingredients, bactericidal ingredients and/or cooling sensation ingredients are included. Specifically, the anti-inflammatory ingredient can be prednisolone acid (PVA) (prodrug steroid) or glycyrrhetinic acid, the anti-itching ingredient can be crotamiton, the skin tissue repair ingredient can be allantoin, the bactericidal ingredient can be isopropyl methylphenol, and the cooling sensation ingredient can be I-menthol.

However, therapeutic drugs assist in reducing the uncomfortable symptoms caused by insufficient sebum. If you want to eliminate the symptoms of discomfort fundamentally, you must focus on the problem of insufficient sebum secretion. Therefore, it is still expected in the market to develop a product that can promote sebaceous glands to secrete lipid.

SUMMARY OF THE INVENTION

The present invention found that derived peptides of lactoferrin (LF) can effectively promote and/or increase the lipid synthesis of sebocytes, and can be used as an alternative solution to solve problems such as too little lipid on the scalp.

In one aspect, the present invention provides a derived peptide of a lactoferrin (LF) for promoting and/or increasing lipid synthesis, wherein the derived peptide of the lactoferrin comprises the amino acid sequence of SEQ ID NO: 01.

Preferably, the promoting and/or increasing lipid synthesis refers the lipid synthesis of a subject's cells is promoted or increased so that a content of a synthesized lipid is increased.

Preferably, an increase ratio of the content of the synthesized lipid to that of a non-administered subject ranges from 10 to 60%.

In another aspect, the present invention provides a composition for promoting and/or increasing lipid synthesis, comprising a derived peptide of a lactoferrin, wherein the derived peptide of the lactoferrin comprises the amino acid sequence of SEQ ID NO: 01.

Preferably, the composition comprises about 5 µg/mL to 1000 µg/mL the derived peptide of the lactoferrin.

Preferably, the composition comprises one or more pharmaceutically acceptable carriers.

Preferably, a dosage form of the composition is an ointment, a gel, a cream, an emulsion, a liquid, a wax, a powder, a spray, a gel spray, a foam, a shampoo, a treatment agent, a scalp treatment agent, a tonic, a drop or a patch.

Preferably, the promoting and/or increasing lipid synthesis refers the lipid synthesis of a subject's cells is promoted or increased so that a content of a synthesized lipid is increased.

Preferably, an increase ratio of the content of the synthesized lipid to that of a non-administered subject ranges from 10 to 60%.

In a further aspect, the present invention provides a method for promoting and/or increasing lipid synthesis, comprising administering the composition as described above to a subject.

Preferably, the promoting and/or increasing lipid synthesis is achieved by administering the composition comprising the derived peptide of the lactoferrin to a subject.

Preferably, an effective amount of the composition administered to the subject ranges from 5 µg/mL to 1000 µg/mL.

Preferably, a route of administering the composition to the subject is transdermal.

Preferably, a frequency of administering the composition to the subject is daily, at least one day apart or weekly.

Preferably, the promoting and/or increasing lipid synthesis refers the lipid synthesis of the subject's cells is promoted or increased so that a content of a synthesized lipid is increased.

Preferably, an increase percentage of the content of the synthesized lipid to that of a non-administered subject ranges from 10 to 60%.

Preferably, the subject's cells refer to sebocytes.

Preferably, the lipid synthesis is induced by linoleic acid.

DETAILED DESCRIPTION OF THE EMBODIMENTS

Figure 1:
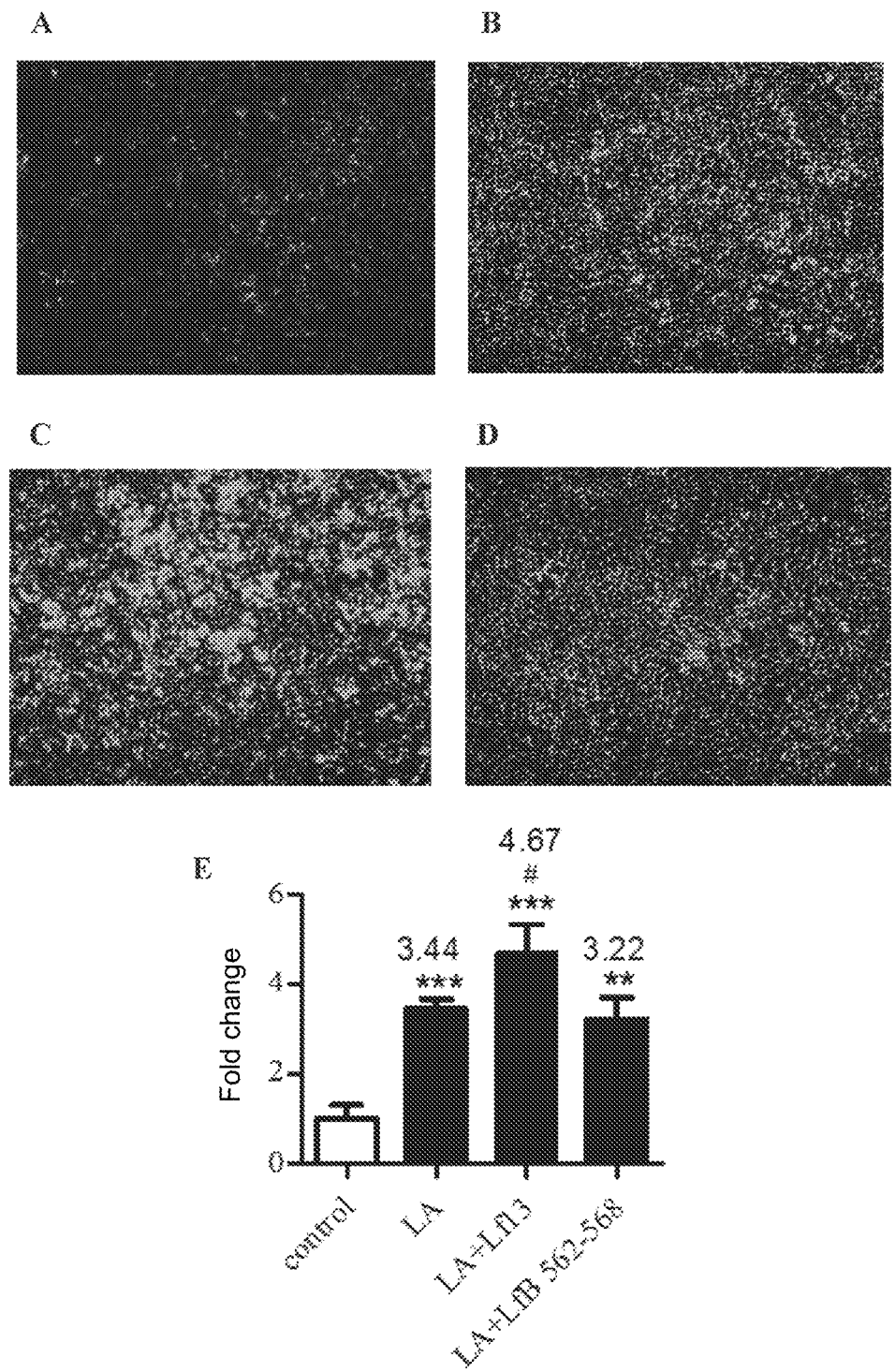
FIG. 1 shows the lipid content of sebocytes in the negative control group, the positive control group, and different types of lactoferrin peptide groups. Photographs of the neutral lipid in the sebocyte stain with Nile red under a fluorescent microscope are shown as A for the negative control group (control), B for the positive control group (LA), C for the lactoferrin peptide Lf13 group (LA+Lf13) and D for the lactoferrin peptide LfB562-568 group (LA+LfB562-568). E is a statistical bar graph of the fluorescence intensity of each group measured by a fluorescent quantifier, in which * shows a significant difference from the negative control group, and # shows a significant difference from the positive control group. The experimental results are shown as the average±standard deviation of three experiments. ***$p<0.001$.###$p<0.001$

Unless otherwise defined, all technical and scientific terms used herein have the same meaning as those understood by people having ordinary skill in the art of the present invention.

When the term "a" or "one" is used together with the term "including" in the claims and/or specification, it means "one", but it also has the same meaning as "one or more", "at least one" and "one or more than one".

The term "peptide" is used herein with its conventional meaning, which means it is a polymer whose monomers are amino acids and are linked to each other by amide bonds. Alternatively, it refers to a polypeptide. When the amino acid is an α-amino acid, L-optical isomer or D-optical isomer can be used. In addition, it may also contain unnatural amino acids such as β-alanine, phenylglycine and homoarginine. The standard abbreviation of amino acids is used.

The term "carrier" as used herein refers to a material that is generally used to prepare pharmaceutical or cosmetic compositions to improve stability, sterility, and delivery. When the peptide delivery system is formulated as a solution or suspension, the delivery system is in an acceptable carrier.

Insufficient sebum in the scalp can cause damage to the epidermal layer or loss of water, and symptoms such as dryness, itching, and roughness of the scalp, dull appearance, erythema, and even desquamation can occur. Although there are therapeutic drugs on the market, they can only assist in reducing the above-mentioned uncomfortable symptoms, and cannot fundamentally solve the problem of insufficient sebum secretion.

In this regard, an object of the present invention is to develop a novel composition, which would not cause other discomfort to the user, such as inflammation, or other diseases or symptoms derived therefrom. This novel composition can also start from the source of the problem to promote the production of sebum.

In view of the above, the present invention develops a derived peptide of a lactoferrin, which can promote the sebaceous glands of the scalp to secrete lipid and/or increase the lipid secretion rate of the sebaceous glands of the scalp. The derived peptide of the lactoferrin can be obtained by chemical synthesis. In one embodiment, the derived peptide of the lactoferrin comprises the amino acid sequence of SEQ ID NO:01.

The present invention also develops a composition, which comprises the derived peptide of the lactoferrin as described above. In one embodiment, the composition comprises the derived peptide of the lactoferrin in an amount of about 5 μg/mL to 1000 μg/mL, preferably about 100 μg/mL to 500 μg/mL, and more preferably about 200 μg/mL to 400 μg/mL.

The composition of the present invention includes a carrier for improving stability, sterility, and delivery without affecting the biological activity of the derived peptide of the lactoferrin. In one embodiment, the composition includes one or more pharmaceutically acceptable carriers. In a preferred embodiment, the acceptable carrier is an aqueous carrier. Various aqueous carriers can be used, such as water, buffer, 0.8% saline, 0.3% glycine, hyaluronic acid and the like. In addition, the composition may contain physiologically acceptable auxiliary substances that can approach physiological conditions as required, such as pH adjusting and buffering agents, solution tension adjusting agents, wetting agents, and the like. Specific examples include sodium acetate, sodium lactate, sodium chloride, potassium chloride, calcium chloride, sorbitan monolaurate, triethanolamine oleate, and the like.

The composition of the present invention, without affecting the biological activity of the derived peptide of the lactoferrin, can be formulated using known and widely used techniques. In one embodiment, the dosage form of the composition is an external agent. The external agent is not particularly limited as long as the composition can be applied, sprayed, or adhered to the part to be administered (affected part) of the skin of the individual to be administered. Examples of external agents include ointments, gels, creams, emulsions, liquids, waxes, powders, sprays, gel sprays, foams, shampoos, treatment agents, scalp treatment agents, tonic, drops or patches. In a preferred embodiment, the dosage form of the composition is an ointment, a gel, a cream, an emulsion, a liquid, a spray, a shampoo, a treatment agent, drops or a patch. The above-mentioned external agents can use the derived peptide of the lactoferrin as active ingredients, and then pharmaceutically acceptable bases or various additives as required can be added as needed.

The ointment preparation of the present invention can be either an oily base or a water-soluble base, and both of them can be easily obtained according to known methods. Oily bases, such as vaseline, have little irritation, and are odorless and excellent in skin protection, softening, scab removal, granulation formation and epithelialization promotion. Although vaseline changes its viscosity and consistency due to temperature and thus has different hardness in winter and summer, it is one of the bases with high safety. Vaseline includes yellow petrolatum and white petrolatum with higher purity, both of which can be used. The water-soluble base is a macrogol-based ointment, which has a strong effect of absorbing and removing aqueous secretions. Ointment (vaseline preparation) can be prepared by dissolving an appropriate amount of the derived peptide of the lactoferrin in distilled water or physiological saline to form an aqueous solution and then further mixing it with known or conventional vaseline and stirring according to the known or conventional methods.

The gel agent (suspension base) of the present invention is a water-containing gel, an anhydrous gel, and a low-water content gel composed of a swellable gel-forming material. Furthermore, the gel agent may also be a hydrogel base or a lyogel base, preferably a transparent hydrogel with inorganic or organic polymers as the base. The gel itself is not absorbed by the skin like preparations containing oil or fat. The hydrogel base is a substance that is fat-free, has an ointment-like consistency, and aims to improve the transdermal absorbability of the drug. The lyogel base is a substance obtained by suspending stearyl alcohol and the like in propylene glycol and gelling, and has excellent transdermal absorbability and hygroscopicity. The gel agent can also be used as a gel spray after being filled in a spray container. The gel agent of the present invention can be obtained by uniformly dispersing the derived peptide of the lactoferrin in a hydrophilic gel base. The hydrophilic gel base includes carboxy vinyl polymer, sodium polyacrylate, (vinyl methyl ether/ethyl maleate) copolymer, polymethacrylate, propylene glycol, and the like. The gel agent may be prepared by dissolving an appropriate amount of the derived peptide of the lactoferrin in distilled water or physiological saline to form an aqueous solution and then further mixing it with known or conventional gel bases and stirring according to known or conventional methods.

The cream (emulsion base) of the present invention may be an oil-in-water base (O/W) (vanishing cream) or a water-in-oil base (W/O) (cold cream). The oil-in-water base has less oil-soluble components than water-soluble components, and has the advantage that the whiteness of the cream disappears when it is applied. The cream has good pushing uniformity, good feeling of use on sweaty skin, excellent cosmetic properties and good skin absorption. The water-in-oil base has less water-soluble components than oil-soluble components, and has a cooling effect when it is applied to and pushed evenly on the skin, so it is also called cold cream.

Compared with ointments or creams, the emulsion of the present invention adheres to the hair and is more suitable for use on hair parts and the like. The type of the emulsion can be any of a suspension emulsion base, an emulsive emulsion, and a solution emulsion base.

The liquid of the present invention is obtained by dissolving the derived peptide of the lactoferrin as an active ingredient in alcohol, propylene glycol, polyethylene glycol, water and the like as a base. In a preferred embodiment, the liquid is composed of an aqueous solution formed by dissolving the derived peptide of the lactoferrin in physiological saline. In the aqueous solution, in addition to physiological saline, a small amount of organic bases, such as alcohol, propylene glycol or polyethylene glycol, may also be mixed.

The spray agent of the present invention is a solution of the derived peptide of the lactoferrin sprayed by gas pressure or hand pressure operation. Spray formulations are more convenient than other formulations when used in a wide range.

The foaming agent of the present invention is made by forming a solution of the derived peptide of the lactoferrin and adding a milder amino acid surfactant therein, and is a spray released in a bubble form. From the viewpoint of scalp adhesion, the foaming agent is excellent in effect.

The shampoo of the present invention is a formulation in which the derived peptide of the lactoferrin is mixed or dissolved in the hair washing emulsion, and can be applied at the same time during shampooing. Since the shampoo contains milder amino acid surfactants, it has the effect of allowing the derived peptide of the lactoferrin to penetrate into the scalp. Especially in the case of excessive sebum secretion, shampoo is advantageous because it can remove excess sebum.

The treatment agent of the present invention is a formulation in which the derived peptide of the lactoferrin is mixed or dissolved in the treatment agent used during hair washing and can be applied at the same time during hair caring. The treatment agent can simultaneously replenish moisture and oil to the scalp when it is applied. The treatment agent is advantageous because it has the functions of moisturizing and replenishing oil to the scalp when being applied.

The scalp treatment agent of the present invention refers to a treatment agent specially formulated with ingredients for moisturizing the scalp and replenishing oil. Most of the scalp treatment agents are blended with various plant extracts, such as rosemary extract, soapberry extract or coconut extract.

The tonic of the present invention can be prepared by formulating the derived peptide of the lactoferrin, and simultaneously formulating the following base materials: 50% to 70% alcohol and water; hinokitiol, panthenol (provitamin B5) or Swertia Japonica extract and other ingredients that have the function of keeping the hair and scalp healthy; dipotassium glycyrrhizinate, which has a female hormone-like action and is formulated with a fungicide, a moisturizing ingredients such as glycerin, salicylic acid that makes dandruff easy to remove, menthol that prevents itching and gives a cooling sensation, fragrance, etc. Tonics are used to prevent dandruff, odor and keep hair clean, while preventing itching, stuffiness and dampness, and eliminating unpleasant symptoms about hair. They are generally used after shampooing.

The composition of the present invention can be applied to the above-mentioned various dosage forms, and other commonly used ingredients, such as thickeners, vitamins, amino acids, anti-wrinkle agents, seaweed extracts, cell activators, transdermal absorption promoters, foaming agents, solubilizers, keratolytic agents, hormones, pigments, plasticizers, inorganic powders, organic powders, etc., can also be appropriately added to these dosage forms according to needs.

According to the above-mentioned derived peptide of the lactoferrin and the composition containing the same, the present invention further develops a use and method for promoting and/or increasing lipid synthesis. The composition of the present invention achieves the effect of promoting and/or increasing lipid synthesis of the subject's cells by administering the composition comprising the derived peptide of the lactoferrin to the subject. In one embodiment, the effective amount of the composition administered to the subject ranges from 5 μg/mL to 1000 μg/mL, preferably 100 μg/mL to 500 μg/mL, and more preferably 200 μg/mL to 400 μg/mL.

The route of the present invention to administer the composition to the subject depends on the type of the composition and the dosage suitable for the subject. In a preferred embodiment, the route of administration is transdermal, for example. The frequency of the present invention to administer the composition to the subject depends on the type of the composition and the dose suitable for the subject. In one embodiment, the frequency of administration is, for example, daily, at least one day apart or weekly, preferably daily.

The composition of the present invention has the effect of promoting and/or increasing lipid synthesis by containing the derived peptide of the lactoferrin. In one embodiment, the promotion of lipid synthesis refers the lipid synthesis of the cells of the individual (the subject) receiving the administration of the composition of the present invention is promoted such that the content of lipid synthesized by the cells of the subject after the administration of the composition is increased compared to that before the administration of the composition. In one embodiment, the increase of lipid synthesis refers the lipid synthesis of the cells of the individual (the subject) receiving the administration of the composition of the present invention is increased such that the content of lipid synthesized by the cells of the subject after the administration of the composition is increased compared to that before the administration of the composition. In one embodiment, the increase percentage of synthesized lipid content is calculated by the following formula: content of lipid synthesized by the cells after the administration of the composition to the subject/content of lipid synthesized by the cells before the administration of the composition to the subject×100%. In one embodiment, the increase percentage of the content of the synthesized lipid is 10-60%, preferably 20-50%, and more preferably 30-40% of the content of the lipid synthesized by the subject without administration of the composition.

The subject to whom the composition of the present invention is administered is a human or an animal, preferably a human. The cells of the subject of the present invention refer to sebocytes. The mechanism of lipid synthesis targeted by the composition of the present invention is not particularly limited. In one embodiment, in the lipid synthesis mechanism targeted by the composition of the present invention, the lipid synthesis is induced by linoleic acid.

The following examples illustrate the experiments conducted in the research and development of the present invention to further clarify the features and advantages of the present invention. It should be understood that the embodiments are only illustrative examples of the claimed invention, and should not be used to limit the scope of the claims of the present invention.

Materials and Methods

1. Sample Preparation

Lactoferrin peptide Lf13 and lactoferrin peptide LfB562-568 were purchased from DgPeptides Co., Ltd (Hangzhou, China). The purity and composition of these lactoferrin peptides were confirmed by high performance liquid chromatography (HPLC) and mass spectrometer. 10 mg of the freeze-dried powder of the peptide was dissolved in 1 mL of double deionized water (dd$H_2O$) and stored at −20° C. for use as a sample of lactoferrin peptide. Nile red was purchased from Sigma-Aldrich Corporation (Missouri, USA). Nile Red was dissolved in 1 mg/mL acetone and used as a dye for later use.

2. Cell Culture

Human sebocytes (Cat. No. 36079-01, Celprogen, Torrance, CA, USA) were cultured in Dulbecco's Modified Eagle Medium (DMEM): Nutrient Mixture F-12 (DMEM/F12) purchased from Thermo Fisher Scientific Limited (Barrington, IL, USA), 10% fetal bovine serum (FBS) purchased from Gibco, Grand Island, NY, USA and penicillin/streptomycin (100 IU/50 g/mL), incubated at 37° C. in the 5% $CO_2$ atmosphere.

3. Neutral Fat Detection

Human sebocytes were implanted in 24- or 96-well plates. After 24 hours of culture, the cells were divided into a negative control group, a positive control group and an experimental group. The negative control group did not receive any treatment, the positive control group was added 0.1 mM linoleic acid (LA), and the experimental group was added 0.1 mM linoleic acid (LA) and 50 to 200 μg/mL lactoferrin peptide Lf13 or 50 μg/mL lactoferrin peptide LfB562-568. The treated human sebocytes were cultured for two days. Human sebocytes were fixed with 4% formaldehyde at room temperature. After 60 minutes of fixation, the cells were washed with PBS and stain with Nile Red solution (1 μg/ml in PBS) at 37° C. for 15 minutes. Next, the cells were washed and observed under a fluorescent microscope. Fluorescence intensity was measured with fluorometer Spectra Max i3.

Experimental Results

FIG. 1 shows the lipid contents of sebocytes in the negative control group, the positive control group, and the experimental groups with 50 μg/mL lactoferrin peptide Lf13 and lactoferrin peptide LfB562-568, respectively. Compared with the negative control group in A, the fluorescence intensity of the positive control group in B increases, indicating that the addition of LA in the positive control group does induce lipid synthesis. The fluorescence intensity of the experimental group in C was increased compared with that of the positive control group in B, indicating that the addition of lactoferrin peptide Lf13 in the experimental group in C could promote and/or increase the lipid synthesis induced by LA, thereby increasing the final lipid content. However, compared with the positive control group in B, the fluorescence intensity of the experimental group in D did not increase significantly, indicating that the addition of the lactoferrin peptide LfB562-568 in the experimental group in D could not significantly promote and/or increase the lipid synthesis induced by LA, and could not greatly increase the final lipid content. The statistical bar graph of the fluorescence intensity of each group E shows that the fluorescence intensity of the negative control group is about 1, the fluorescence intensity of the positive control group is about 3.44, the fluorescence intensity of the lactoferrin peptide Lf13 in the experimental group is about 4.67, and the fluorescence intensity of the lactoferrin peptide LfB562-568 in the experimental group is about 3.22. Compared with the negative control group, the fluorescence intensity of the positive control group shows ***, indicating that there is a significant difference in the content of lipid synthesized by the induction of added LA, and the lipid content is more than 3 times. Compared with the positive control group, the fluorescence intensity of the lactoferrin peptide Lf13 of the experimental group shows #, indicating that the addition of lactoferrin peptide Lf13 can promote and/or increase the content of lipid synthesized by the induction of LA, there is a significant difference in the lipid content, and the lipid content is increase d by 40%. Compared with the positive control group, the fluorescence intensity of the lactoferrin peptide LfB562-568 in the experimental group does not show #, indicating that the addition of lactoferrin LfB562-568 has no significant difference in promoting and/or increasing the content of lipid synthesized by the induction of LA. It can be seen that not all lactoferrin peptides can promote and/or increase the content of synthesized lipid, and whether the lactoferrin peptide can promote and/or increase the content of synthesized lipid must be confirmed through experiments.

Figure 2:
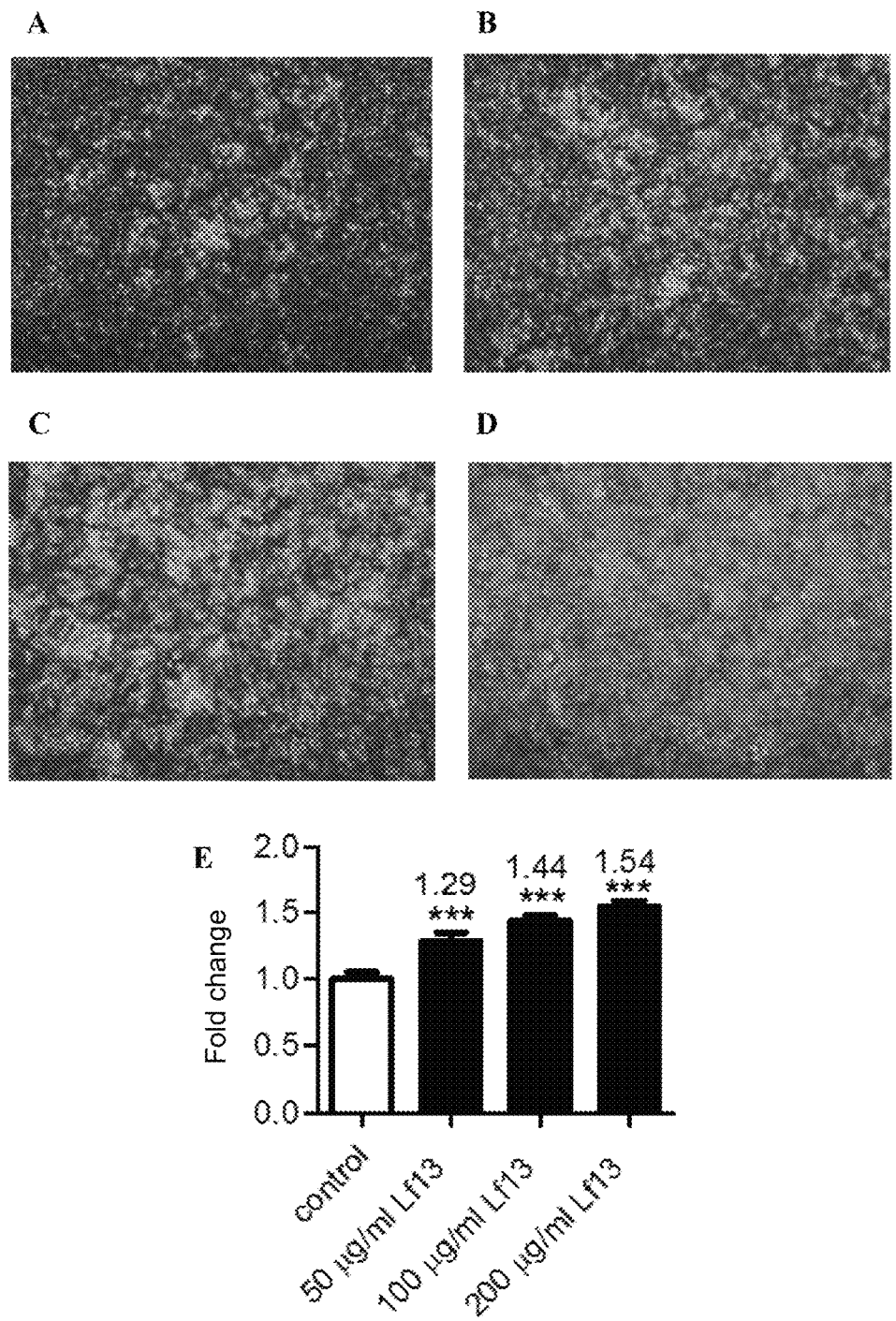
FIG. 2 shows the lipid content of sebocytes in the negative control group with different concentrations of lactoferrin peptides. Photographs of the neutral lipid in the sebocyte stain with Nile red under a fluorescent microscope are shown as A for the negative control group (control), B for the group of lactoferrin peptide Lf13 with a concentration of 50 μg/ml (50 μg/ml Lf13), C for the group of lactoferrin peptide Lf13 with a concentration of 100 μg/ml (100 μg/ml+Lf13) and D for the group of lactoferrin peptide Lf13 with a concentration of 200 μg/ml (200 μg/ml+Lf13). E is a statistical bar graph of the fluorescence intensity of each group measured by a fluorescent quantifier, in which * shows a significant difference from the negative control group. The experimental results are shown as the average±standard deviation of three experiments. ***p<0.001

FIG. 2 shows the lipid contents of sebocytes in the negative control group and the experimental groups with 50 μg/mL, 100 μg/mL and 200 μg/mL lactoferrin peptide Lf13 respectively. Compared with the negative control group in A, the fluorescence intensity of lactoferrin peptide Lf13 at 50 μg/mL in experimental group in B increases, indicating that the addition of lactoferrin peptide Lf13 in the experimental group can promote and/or increase the synthesis of lipid, thereby increasing the final lipid content. The fluorescence intensity of lactoferrin peptide Lf13 at 100 μg/mL in experimental group in C increases compared with that of experimental group in B, and the fluorescence intensity of lactoferrin peptide Lf13 at 200 μg/mL in experimental group in D increases compared with that of experimental group in C, indicating that the higher the concentration of the lactoferrin peptide is in the experimental group, the more the amount of lipid is promoted and/or increased. The statistical bar graph of the fluorescence intensity of each group in E shows that the fluorescence intensity of the negative control group is about 1.0, the fluorescence intensity of the lactoferrin peptide Lf13 at 50 μg/mL in the experimental group is about 1.29, the fluorescence intensity of the lactoferrin peptide Lf13 at 100 μg/mL in the experimental group is about 1.44, and the fluorescence intensity of the lactoferrin peptide Lf13 at 400 μg/mL in the experimental group is about 1.54. Compared with the negative control group, the fluorescence intensity of the experimental group shows ***, indicating that the addition of lactoferrin peptide Lf13 can promote and/or increase the content of lipid, there is a significant difference in the lipid contents, and the lipid content is increased by 20% to 50%. In addition, as the concentration of the added lactoferrin peptide Lf13 increases, the lipid content increases, indicating that the lactoferrin peptide Lf13 promotes and/or increases the lipid content in a dose-dependent manner.

People having ordinary skill in the art will understand that the above specific embodiments can be modified without departing from the broad inventive concept of the present invention. Therefore, it should be understood that the present invention is not limited to the specific embodiments disclosed, but is intended to cover those modifications within the spirit and scope of the present invention as defined by the appended claims.

What is claimed is:

1. A method for promoting and/or increasing lipid synthesis, comprising
administering a peptide consisting of the amino acid sequence of SEQ ID NO: 01 to a subject's sebocyte cell,
wherein the lipid content of the subject's sebocyte cell administered the peptide is 10 to 60% higher than that of non-administrated subject's sebocyte cell.

2. The method of claim 1, wherein an effective amount of the peptide administered to the subject's sebocyte cell ranges from 5 μg/mL to 1000 μg/mL.

3. The method of claim 1, wherein a route of administering the peptide to the subject's sebocyte cell is transdermal.

4. The method of claim 1, wherein a frequency of administering the peptide to the subject's sebocyte cell is daily, at least one day apart or weekly.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Lactoferrin derived peptide

<400> SEQUENCE: 1

```
Ala Pro Arg Lys Asn Val Arg Trp Cys Thr Ile Ser Gln
1               5                   10
```